US012089940B2

(12) United States Patent
Hoitink et al.

(10) Patent No.: US 12,089,940 B2
(45) Date of Patent: *Sep. 17, 2024

(54) CATHETER WITH HIGH DENSITY ELECTRODE SPINE ARRAY

(71) Applicant: BIOSENSE WEBSTER (ISRAEL) LTD., Yokneam (IL)

(72) Inventors: Ryan Hoitink, Pasadena, CA (US); Curt R. Eyster, Alta Loma, CA (US); Stuart Williams, Ontario, CA (US); Meir Bar-Tal, Haifa (IL); Shubhayu Basu, Anaheim, CA (US); Shamim Qutubuddin, Chino Hills, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 286 days.

This patent is subject to a terminal disclaimer.

(21) Appl. No.: 17/392,522

(22) Filed: Aug. 3, 2021

(65) Prior Publication Data
US 2021/0361216 A1 Nov. 25, 2021

Related U.S. Application Data

(60) Continuation of application No. 16/827,711, filed on Mar. 24, 2020, now Pat. No. 11,083,400, which is a
(Continued)

(51) Int. Cl.
*A61B 5/287* (2021.01)
*A61B 5/00* (2006.01)
(Continued)

(52) U.S. Cl.
CPC ............ *A61B 5/287* (2021.01); *A61B 5/6858* (2013.01); *A61B 5/6859* (2013.01);
(Continued)

(58) Field of Classification Search
CPC ................ A61B 18/1492; A61B 2018/00839
See application file for complete search history.

(56) References Cited

U.S. PATENT DOCUMENTS

| 4,522,212 A | 6/1985 | Gelinas et al. |
| 4,529,912 A | 7/1985 | Northrup et al. |
| (Continued) | | |

FOREIGN PATENT DOCUMENTS

| AU | 2015202258 A1 | 5/2015 |
| AU | 2016204351 A1 | 1/2017 |
| (Continued) | | |

OTHER PUBLICATIONS

Chuwei Z., et al., "Fixation of Internal Jugular Vein Catheter to ECG Electrode with Sutures for Hemodialysis," Journal of Nursing Science, Sep. 2012, vol. 27 (17), 9 pages.
(Continued)

*Primary Examiner* — Eun Hwa Kim
(74) *Attorney, Agent, or Firm* — Etan S. Chatlynne; Calderon Safran & Wright P.C.

(57) ABSTRACT

A catheter adapted or high density mapping and/or ablation of tissue surface has a distal electrode matrix having a plurality of spines arranged in parallel configuration on which a multitude of electrodes are carried in a grid formation for providing uniformity and predictability in electrode placement on the tissue surface. The matrix can be dragged against the tissue surface upon deflection (and/or release of the deflection) of the catheter. The spines generally maintain their parallel configuration and the multitude of electrodes generally maintain their predetermined relative spacing in the grid formation as the matrix is dragged across the tissue surface in providing very high density mapping signals. The
(Continued)

spines may have free distal ends, or distal ends that are joined to form loops for maintaining the spines in parallel configuration.

15 Claims, 12 Drawing Sheets

Related U.S. Application Data continuation of application No. 15/818,550, filed on Nov. 20, 2017, now Pat. No. 10,595,740, which is a division of application No. 14/549,457, filed on Nov. 20, 2014, now Pat. No. 9,820,664.

(51) Int. Cl.
*A61B 18/14* (2006.01)
*A61B 18/00* (2006.01)

(52) U.S. Cl.
CPC ............... *A61B 18/1492* (2013.01); *A61B 2018/00267* (2013.01); *A61B 2018/00357* (2013.01); *A61B 2018/00577* (2013.01); *A61B 2018/00839* (2013.01); *A61B 2018/1467* (2013.01); *A61B 2562/222* (2013.01)

(56) References Cited

U.S. PATENT DOCUMENTS

| | | | |
|---|---|---|---|
| 5,702,438 A | 12/1997 | Avitall |
| 5,964,757 A | 10/1999 | Ponzi |
| 6,029,091 A | 2/2000 | De La Rama et al. |
| 6,071,279 A | 6/2000 | Whayne et al. |
| 6,071,280 A | 6/2000 | Edwards et al. |
| 6,071,282 A | 6/2000 | Fleischman |
| 6,123,699 A | 9/2000 | Webster, Jr. |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,210,407 B1 | 4/2001 | Webster |
| 6,267,746 B1 | 7/2001 | Bumbalough |
| 6,415,187 B1 | 7/2002 | Kuzma et al. |
| 6,522,932 B1 | 2/2003 | Kuzma et al. |
| 6,652,515 B1 | 11/2003 | Maguire et al. |
| 6,658,302 B1 | 12/2003 | Kuzma et al. |
| 6,961,602 B2 | 11/2005 | Fuimaono et al. |
| 7,027,851 B2 | 4/2006 | Mejia |
| 7,089,045 B2 | 8/2006 | Fuimaono et al. |
| 7,099,712 B2 | 8/2006 | Fuimaono et al. |
| 7,228,164 B2 | 6/2007 | Fuimaono et al. |
| 7,257,435 B2 | 8/2007 | Plaza |
| 7,412,274 B2 | 8/2008 | Mejia |
| 7,429,261 B2 | 9/2008 | Kunis et al. |
| 7,561,907 B2 | 7/2009 | Fuimaono et al. |
| 8,187,267 B2 | 5/2012 | Pappone et al. |
| 8,206,404 B2 | 6/2012 | De La Rama et al. |
| 8,271,099 B1 | 9/2012 | Swanson |
| 8,391,947 B2 | 3/2013 | Urman et al. |
| 8,486,063 B2 | 7/2013 | Werneth et al. |
| 8,565,894 B2 | 10/2013 | Vetter et al. |
| 8,603,069 B2 | 12/2013 | Selkee |
| 8,734,440 B2 | 5/2014 | Wu |
| 8,744,599 B2 | 6/2014 | Tegg |
| 8,974,454 B2 | 3/2015 | De La Rama et al. |
| 8,979,837 B2 | 3/2015 | De La Rama et al. |
| 9,044,245 B2 | 6/2015 | Condie et al. |
| 9,392,971 B2 | 7/2016 | Asirvatham et al. |
| 9,820,664 B2 | 11/2017 | Hoitink et al. |
| 9,833,608 B2 | 12/2017 | Masson |
| 9,907,480 B2 | 3/2018 | Basu et al. |
| 10,220,187 B2 | 3/2019 | De La Rama et al. |
| 10,576,244 B2 | 3/2020 | De La Rama et al. |
| 10,595,740 B2 | 3/2020 | Hoitink et al. |
| 2002/0087058 A1 | 7/2002 | Fuimaono et al. |
| 2003/0130572 A1 | 7/2003 | Phan et al. |
| 2005/0159741 A1 | 7/2005 | Paul et al. |
| 2006/0074412 A1 | 4/2006 | Zerfas et al. |
| 2009/0198300 A1 | 8/2009 | Zhang et al. |
| 2009/0240248 A1 | 9/2009 | Deford et al. |
| 2010/0087848 A1 | 4/2010 | Kim et al. |
| 2010/0286684 A1 | 11/2010 | Hata et al. |
| 2011/0106075 A1 | 5/2011 | Jimenez |
| 2011/0118726 A1 | 5/2011 | De La Rama et al. |
| 2012/0010490 A1 | 1/2012 | Kauphusman et al. |
| 2012/0271302 A1 | 10/2012 | Behl et al. |
| 2012/0296232 A1 | 11/2012 | Ng |
| 2013/0006238 A1 | 1/2013 | Ditter et al. |
| 2013/0053841 A1 | 2/2013 | Grunewald |
| 2013/0172715 A1 | 7/2013 | Just et al. |
| 2013/0253504 A1 | 9/2013 | Fang |
| 2013/0274582 A1 | 10/2013 | Afonso et al. |
| 2014/0200639 A1 | 7/2014 | De La Rama |
| 2014/0249609 A1 | 9/2014 | Zarsky et al. |
| 2014/0296902 A1 | 10/2014 | Huszar et al. |
| 2014/0316496 A1 | 10/2014 | Masson et al. |
| 2014/0350564 A1 | 11/2014 | Huszar et al. |
| 2015/0105645 A1 | 4/2015 | Subramaniam et al. |
| 2015/0112329 A1 | 4/2015 | Ng |
| 2015/0141785 A1 | 5/2015 | Hayam et al. |
| 2015/0351652 A1 | 12/2015 | Marecki et al. |
| 2015/0374252 A1 | 12/2015 | De La Rama et al. |
| 2016/0143588 A1 | 5/2016 | Hoitink et al. |
| 2016/0213916 A1 | 7/2016 | De La Rama |
| 2016/0317094 A1 | 11/2016 | Byrd et al. |
| 2016/0331471 A1 | 11/2016 | Deno et al. |
| 2016/0374582 A1 | 12/2016 | Wu et al. |
| 2016/0374753 A1 | 12/2016 | Wu et al. |
| 2017/0000365 A1 | 1/2017 | Wu et al. |
| 2017/0042449 A1 | 2/2017 | Deno et al. |
| 2017/0049348 A1 | 2/2017 | Deno et al. |
| 2017/0112404 A1 | 4/2017 | De La Rama et al. |
| 2017/0112405 A1 | 4/2017 | Sterrett et al. |
| 2017/0319269 A1 | 11/2017 | Oliverius et al. |
| 2017/0367756 A1 | 12/2017 | Sliwa et al. |
| 2018/0050190 A1 | 2/2018 | Masson |
| 2018/0070845 A1 | 3/2018 | Hoitink et al. |
| 2018/0116539 A1 | 5/2018 | Olson et al. |

FOREIGN PATENT DOCUMENTS

| | | |
|---|---|---|
| AU | 2016204353 A1 | 1/2017 |
| AU | 2016204355 A1 | 1/2017 |
| CA | 2934209 A1 | 12/2016 |
| CA | 2934211 A1 | 12/2016 |
| CA | 2934214 A1 | 12/2016 |
| CN | 1323180 A | 11/2001 |
| CN | 101304778 A | 11/2008 |
| CN | 101687093 A | 3/2010 |
| CN | 101797181 A | 8/2010 |
| CN | 101856271 A | 10/2010 |
| CN | 102292044 A | 12/2011 |
| CN | 102448358 A | 5/2012 |
| CN | 102551704 A | 7/2012 |
| CN | 102639077 A | 8/2012 |
| CN | 102711645 A | 10/2012 |
| CN | 102846374 A | 1/2013 |
| CN | 102895028 A | 1/2013 |
| CN | 102961183 A | 3/2013 |
| CN | 103027677 A | 4/2013 |
| CN | 103281978 A | 9/2013 |
| CN | 103547213 A | 1/2014 |
| CN | 103889348 A | 6/2014 |
| CN | 103908336 A | 7/2014 |
| CN | 203693745 U | 7/2014 |
| CN | 104010585 A | 8/2014 |
| CN | 101797181 B | 12/2015 |
| CN | 102961183 B | 8/2016 |
| CN | 105960201 A | 9/2016 |
| CN | 106264715 A | 1/2017 |
| CN | 106264716 A | 1/2017 |
| CN | 106308790 A | 1/2017 |
| CN | 103315806 B | 6/2017 |

(56) References Cited

FOREIGN PATENT DOCUMENTS

| | | |
|---|---|---|
| CN | 103417290 B | 8/2018 |
| EP | 0856291 A2 | 8/1998 |
| EP | 0779059 B1 | 4/2004 |
| EP | 2664295 A1 | 11/2013 |
| EP | 2732843 A1 | 5/2014 |
| EP | 2752153 A1 | 7/2014 |
| EP | 2907462 A1 | 8/2015 |
| EP | 3023052 A1 | 5/2016 |
| EP | 3111871 A1 | 1/2017 |
| EP | 3111872 A1 | 1/2017 |
| EP | 3114987 A1 | 1/2017 |
| IN | 201614021431 A | 12/2016 |
| IN | 201614021432 A | 12/2016 |
| IN | 201614021450 A | 12/2016 |
| JP | 2003510160 A | 3/2003 |
| JP | 2003290247 A | 10/2003 |
| JP | 2011147802 A | 8/2011 |
| JP | 2011172785 A | 9/2011 |
| JP | 2012130392 A | 7/2012 |
| JP | 2013192948 A | 9/2013 |
| JP | 2014004368 A | 1/2014 |
| JP | 2014506171 A | 3/2014 |
| JP | 2015100706 A | 6/2015 |
| JP | 2015112484 A | 6/2015 |
| JP | 2016104129 A | 6/2016 |
| JP | 2017012750 A | 1/2017 |
| JP | 2017012755 A | 1/2017 |
| JP | 2017038919 A | 2/2017 |
| JP | 2017515436 A | 6/2017 |
| JP | 2018519934 A | 7/2018 |
| JP | 2018537151 A | 12/2018 |
| RU | 2016125763 A | 1/2018 |
| WO | 2004015761 A1 | 2/2004 |
| WO | 2013028998 A2 | 2/2013 |
| WO | 2014022436 A1 | 2/2014 |
| WO | 2014113612 A1 | 7/2014 |
| WO | 2014168987 A1 | 10/2014 |
| WO | 2014172398 A1 | 10/2014 |
| WO | 2015044086 A1 | 4/2015 |
| WO | 2015057521 A1 | 4/2015 |
| WO | 2015095577 A1 | 6/2015 |
| WO | 2015130824 A1 | 9/2015 |
| WO | 2016001015 A1 | 1/2016 |

OTHER PUBLICATIONS

European Examination Report in corresponding European Application No. 15195293.4, dated Jan. 19, 2017, 6 pages.

European Search Report for European Application No. 15195293.4, dated Apr. 12, 2016, 5 pages.

Extended European Search Report for Application No. 19164969.8 dated Jul. 19, 2019, 11 pages.

Extended European Search Report for European Application No. 16176559.9, dated Nov. 7, 2016, 6 pages.

Extended European Search Report for European Application No. 16176598.7, dated Nov. 7, 2016, 4 pages.

Extended European Search Report for European Application No. 16176803.1, dated Dec. 12, 2016, 5 pages.

Extended European Search Report for European Application No. 18166678, dated Jun. 28, 2018, 8 pages.

Israeli Patent Application No. 246414, filed on Jun. 23, 2016, 2 pages (English Abstract attached—also corresponds to US20160374753).

Israeli Patent Application No. 246415, filed on Jun. 23, 2016, 2 pages (English Abstract attached—also corresponds to US20160374582).

Israeli Patent Application No. 246416, filed on Jun. 23, 2016, 2 pages (English Abstract attached—also corresponds to US20170000365).

Office Action for European Application No. 15195293.4, dated Jul. 20, 2017, 5 pages.

Speidel M.A., et al., "Three-dimensional Tracking of Cardiac Catheters using an Inverse Geometry x-ray Fluoroscopy System," Medical Physics, Dec. 2010, vol. 37 (12), pp. 6377-6389.

Extended European Search Report for European Application No. EP22195201.3, dated Jan. 17, 2023, 09 pages.

CATHETER WITH HIGH DENSITY ELECTRODE SPINE ARRAY

CROSS-REFERENCE TO RELATED APPLICATION(S)

The present application is a Continuation Application under 35 U.S.C. § 120 of U.S. patent application Ser. No. 16/827,711, filed Mar. 24, 2020, which is a Continuation Application under 35 U.S.C. § 120 of U.S. patent application Ser. No. 15/818,550, filed Nov. 20, 2017, issued as U.S. Pat. No. 10,595,740, which is a Divisional Application under 35 U.S.C. § 121 of U.S. patent application Ser. No. 14/549,457, filed Nov. 20, 2014, now U.S. Pat. No. 9,820,664. The entire contents of these applications are incorporated by reference herein in their entirety.

FIELD OF INVENTION

This invention relates to catheters, in particular, intravascular catheters for tissue diagnostics and ablation.

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in the tissue region, for example, one of the atria or one of the ventricles. Regardless of the sources, unwanted signals are conducted elsewhere through heart tissue where they can initiate or continue arrhythmia.

Procedures for treating arrhythmia include surgically disrupting the origin of the signals causing the arrhythmia, as well as disrupting the conducting pathway for such signals. More recently, it has been found that by mapping the electrical properties of the endocardium and the heart volume, and selectively ablating cardiac tissue by application of energy, it is possible to cease or modify the propagation of unwanted electrical signals from one portion of the heart to another. The ablation process destroys the unwanted electrical pathways by formation of non-conducting lesions.

In this two-step procedure—mapping followed by ablation—electrical activity at points in the heart is typically sensed and measured by advancing a catheter containing one or more electrical sensors into the heart, and acquiring data at a multiplicity of points. These data are then utilized to select the target areas at which ablation is to be performed.

For greater mapping resolution, it is desirable for a mapping catheter to provide very high density signal maps through the use of a multitude of electrodes sensing electrical activity within a small area, for example, a square centimeter. For mapping within an atria or a ventricle (for example, an apex of a ventricle), it is desirable for a catheter to collect larger amounts of data signals within shorter time spans. It is also desirable for such a catheter to be adaptable to different tissue surfaces, for example, flat, curved, irregular or nonplanar surface tissue and be collapsible for atraumatic advancement and withdrawal through a patient's vasculature.

SUMMARY OF THE INVENTION

The catheter of the present invention is intended to allow high density mapping and/or ablation of tissue surface in the heart, including an atria or a ventricle, by means of a distal electrode matrix having a plurality of spines arranged in parallel configuration on which a multitude of electrodes are carried in a grid formation for providing uniformity and predictability in electrode placement on the tissue surface. The catheter is configured to allow the matrix to be dragged against the tissue surface upon deflection (and/or release of the deflection) of the catheter as actuated by a user manipulating a deflection control handle of the catheter. Advantageously, the spines generally maintain their parallel configuration and the multitude of electrodes generally maintain their predetermined relative spacing in the grid formation as the matrix is dragged across the tissue surface in providing very high density mapping signals.

In some embodiments, the catheter of the present invention comprises an elongated catheter body and a distal electrode matrix having a plurality of spines that carry a multitude of electrodes having a predetermined spatial relationship. The electrode-carrying spines extend generally in a single common plane and have distal portions that are generally parallel to each other in the single common plane so that the predetermined spatial relationship of the electrodes, including spacing between the electrodes on different spines, is generally maintained, especially during electrical sensing of the tissue surface while the spines are dragged along the tissue surface with purposeful deflection (and/or release of deflection) of the catheter as controlled by the user.

In a more detailed embodiment, each spine has a proximal portion, wherein the proximal portions converge at their proximal ends near the distal end of the intermediate deflection section, with each proximal portion spreading outwardly from a longitudinal axis of the catheter, wherein inner spines extend at a lesser angle and outer spines extend at a greater angle from the longitudinal axis, so that the distal portion of each spine is spaced apart from each other and generally parallel with the longitudinal axis.

In a more detailed embodiment, the catheter includes an intermediate deflection section extending between the catheter body and the distal electrode matrix, which is responsive to the control handle for selectively deflecting one side or the other side of the matrix toward the catheter. The deflection enables the selected side of the distal electrode matrix to lie against the tissue surface and maximizing electrode contact with the tissue surface for high density mapping signals with greater regularity, consistency and predictability. The distal electrode matrix includes a plurality of electrodes ranging between about 20 and 44, and preferably between about 28-36 electrodes, and preferably about 32 electrodes.

In a more detailed embodiment, each spine of the distal electrode matrix includes an elongated shape-memory member, a nonconductive covering and at least one ring electrode, wherein a proximal end of each spine is anchored in a connector member extending between the spines and the intermediate deflection section.

The present invention is also directed to a method of using the catheter of the present invention, including laying the distal electrode matrix generally flat against a tissue surface such that the spines of the matrix are in a parallel arrangement, and dragging the distal electrode matrix along the tissue surface in a direction generally parallel with the parallel arrangement of the matrix. The dragging the distal electrode matrix may include maintaining the parallel arrangement of the matrix and/or maintaining at least portion of the matrix flat on the tissue surface. The dragging the distal electrode matrix may also include maintaining a predetermined relative spacing of the electrodes on the matrix. Notably, "against," "on," "laying," and "lying" are used herein without limiting the relative orientation of the distal electrode matrix and the tissue surface, including, for example, whether one or the other of the matrix and tissue surface is above, below or next to the other.

In a detailed embodiment, wherein the distal electrode matrix has a first side and a second side, the method of the present invention includes positioning the distal electrode matrix on the tissue surface with the first side lying against the tissue surface, with at least the intermediate section 14 in its neutral, undeflected state being generally perpendicular to the tissue surface, and deflecting the matrix first side toward the catheter so as to drag the first side of across the tissue surface. The deflecting so as to drag may include maintaining contact between the tissue surface and at least a portion of the electrodes carried on the distal electrode matrix.

In another detailed embodiment, wherein the distal electrode matrix has a first side and a second side, the method includes deflecting the first side of the distal electrode matrix toward the catheter, positioning at least a distal portion of the catheter body 12 generally parallel with the tissue surface, placing the second side of the distal electrode matrix against the tissue surface, and releasing deflection of the first side so as to drag the second surface of the distal electrode matrix across the tissue surface. The releasing deflection so as to drag may include maintaining contact between the tissue surface and at least a portion of the electrodes carried on the distal electrode matrix.

In yet another embodiment, the distal electrode matrix have spines with linear portions in a configuration wherein the linear portions are spaced apart at predetermined separation distances, and the spines are arranged in closed formations at their distal ends to help maintain the linear portions at such predetermined separation distances. In one detailed embodiment, the spines angle inwardly distal of the linear portions and the distal ends are joined with each other. In another detailed embodiment, pairs of spines are formed from single continuous members which are turned back toward their proximal ends to form loops with U-shaped or V-shaped distal ends which also help maintain the linear portions at their predetermined separation distances. The loops may be nonintersecting with a smaller loop inside a larger loop, or be generally the same size but intersecting at one or more locations.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
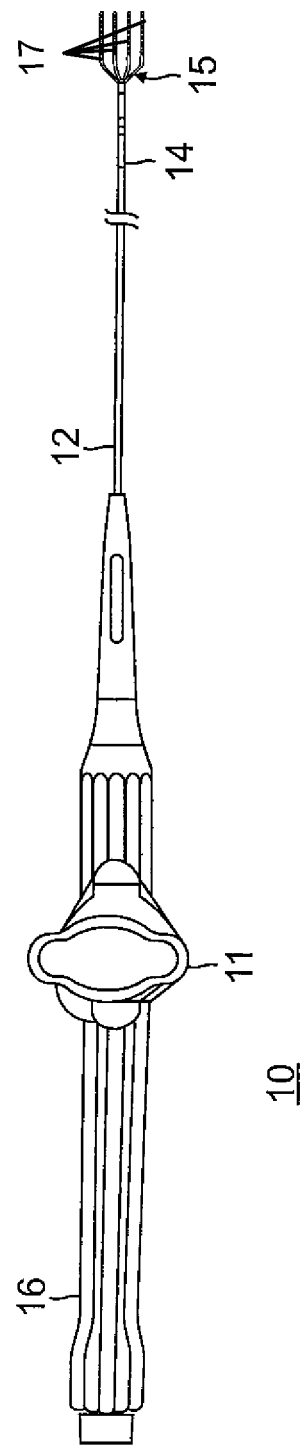
FIG. 1 is a perspective view of a catheter of the present invention, in accordance with some embodiments.

As shown in FIG. 1, the catheter 10 comprises an elongated catheter body 12, an intermediate deflection section 14, a distal electrode assembly or matrix 15, and a deflection control handle 16 attached to the proximal end of the catheter body 12. In accordance with a feature of the present invention, the distal electrode matrix 15 has a plurality of spines 17 that generally lie within a common plane akin to a broom having bristles that generally lie within a common plane.

Figure 2A:
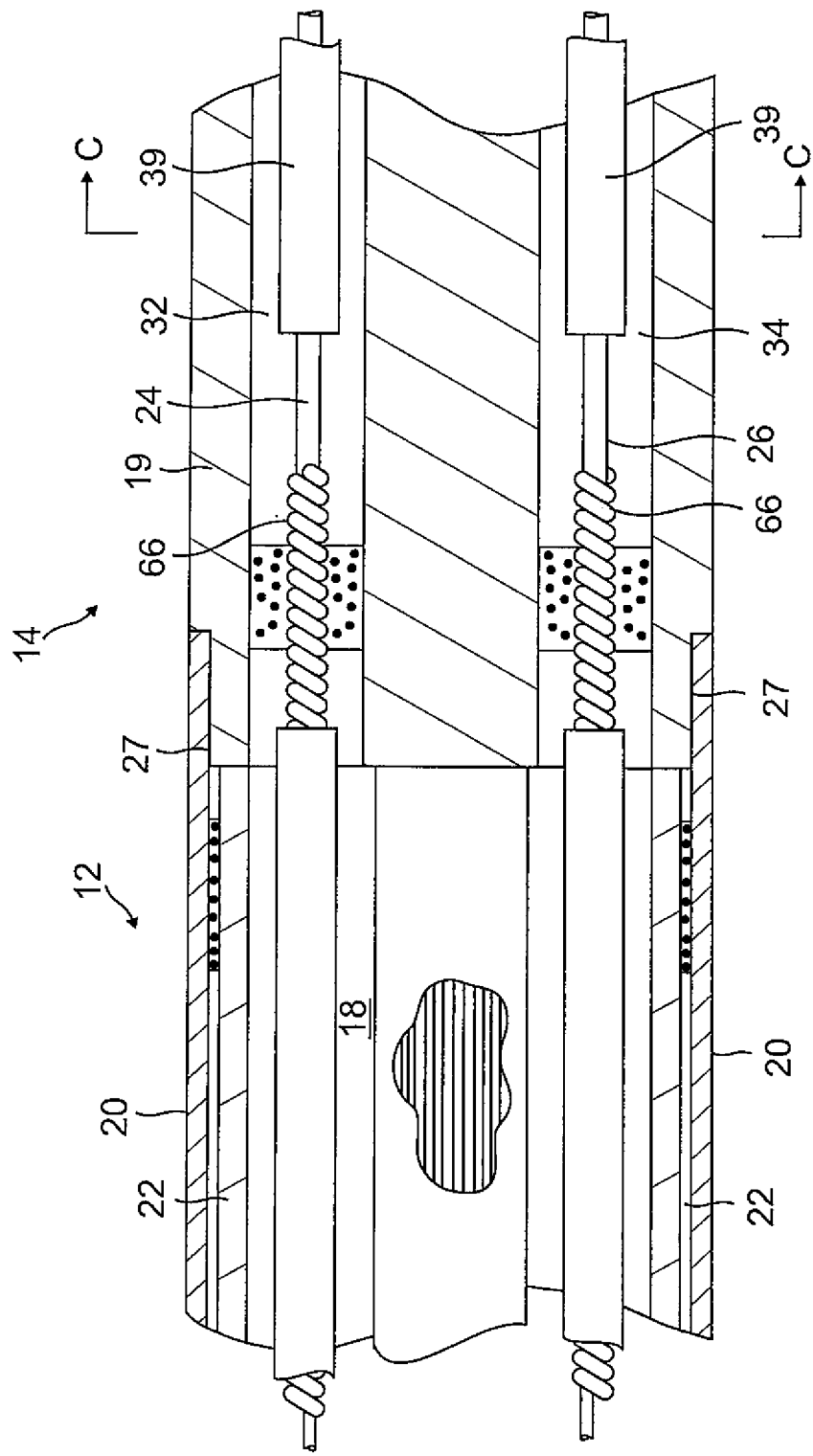
FIG. 2A is a side cross-sectional view of the catheter of FIG. 1, including a junction between a catheter body and a deflection section, taken along a first diameter.
Figure 2B:
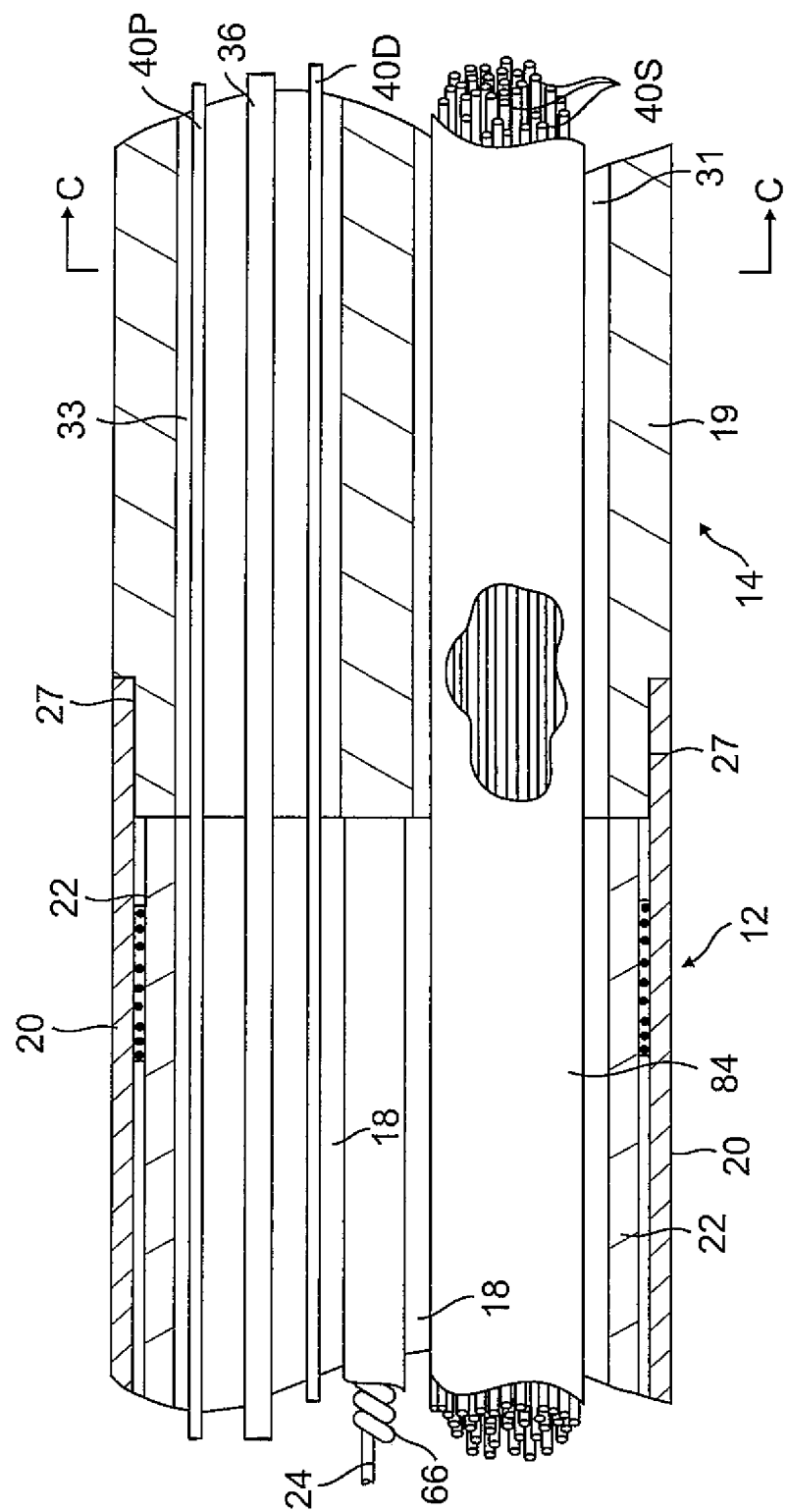
FIG. 2B is a side cross-sectional view of the catheter of FIG. 1, including the junction of FIG. 2A, taken along a second diameter generally perpendicular to the first diameter.

With reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. In some embodiments, the catheter body 12 comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably about 7 french. Likewise, the thickness of the outer wall 20 is not critical, but is thin enough so that the central lumen 18 can accommodate a puller wire, one or more lead wires, and any other desired wires, cables or tubes. If desired, the inner surface of the outer wall 20 is lined with a stiffening tube 22 to provide improved torsional stability. In some embodiments, the outer wall 20 has an outer diameter of from about 0.090 inch to about 0.94 inch and an inner diameter of from about 0.061 inch to about 0.065 inch.

Figure 2C:
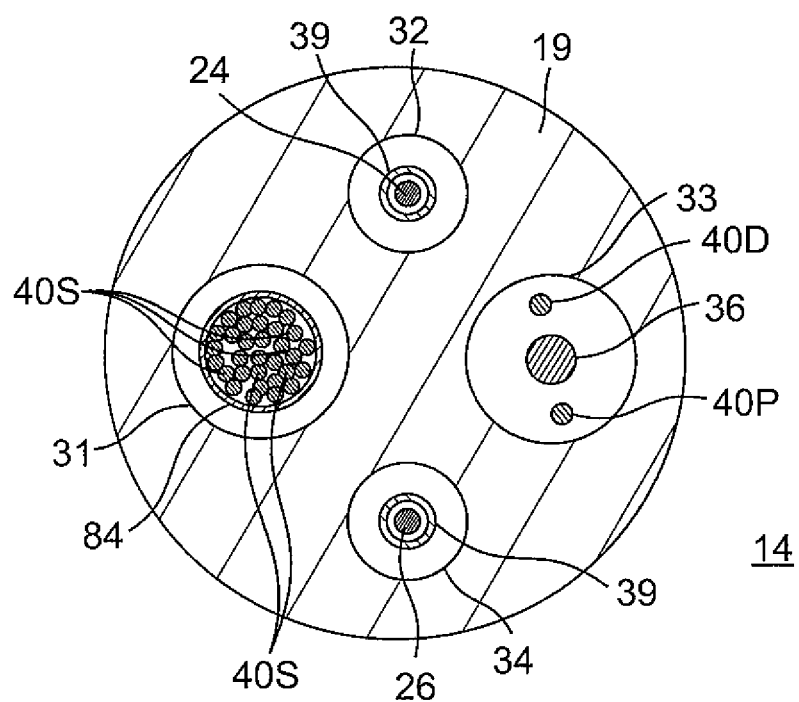
FIG. 2C is an end cross-sectional view of the deflection section of FIGS. 2A and 2B, taken along line C-C.

As shown in FIGS. 2A, 2B and 2C, the intermediate section 14 comprises a shorter section of tubing 19 having multiple lumens, for example, four off-axis lumens 31, 32, 33 and 34. The first lumen 31 carries a plurality of lead wires 40S for ring electrodes 37 carried on the spines 17. The second lumen 32 carries a first puller wire 24. The third lumen 33 carries a cable 36 for an electromagnetic position sensor 42 and a plurality of lead wires 40D and 40P for distal and proximal ring electrodes 38D and 38P carried on the catheter proximally of the distal electrode matrix 15. The fourth lumen 34 (for example, diametrically opposite of the second lumen 32 in the illustrated embodiment) carries a second puller wire 26. The tubing 19 is made of a suitable non-toxic material that is preferably more flexible than the catheter body 12. One suitable material for the tubing 19 is braided polyurethane, i.e., polyurethane with an embedded mesh of braided stainless steel or the like. The size of each lumen is not critical, but is sufficient to house the lead wires, puller wires, the cable and any other components.

The useful length of the catheter, i.e., that portion that can be inserted into the body excluding the distal electrode matrix 15, can vary as desired. Preferably the useful length ranges from about 110 cm to about 120 cm. The length of the intermediate section 14 is a relatively smaller portion of the useful length, and preferably ranges from about 3.5 cm to about 10 cm, more preferably from about 5 cm to about 6.5 cm.

A means for attaching the catheter body 12 to the intermediate section 14 is illustrated in FIGS. 2A and 2B. The proximal end of the intermediate section 14 comprises an outer circumferential notch 27 that receives the inner surface of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Figure 3A:
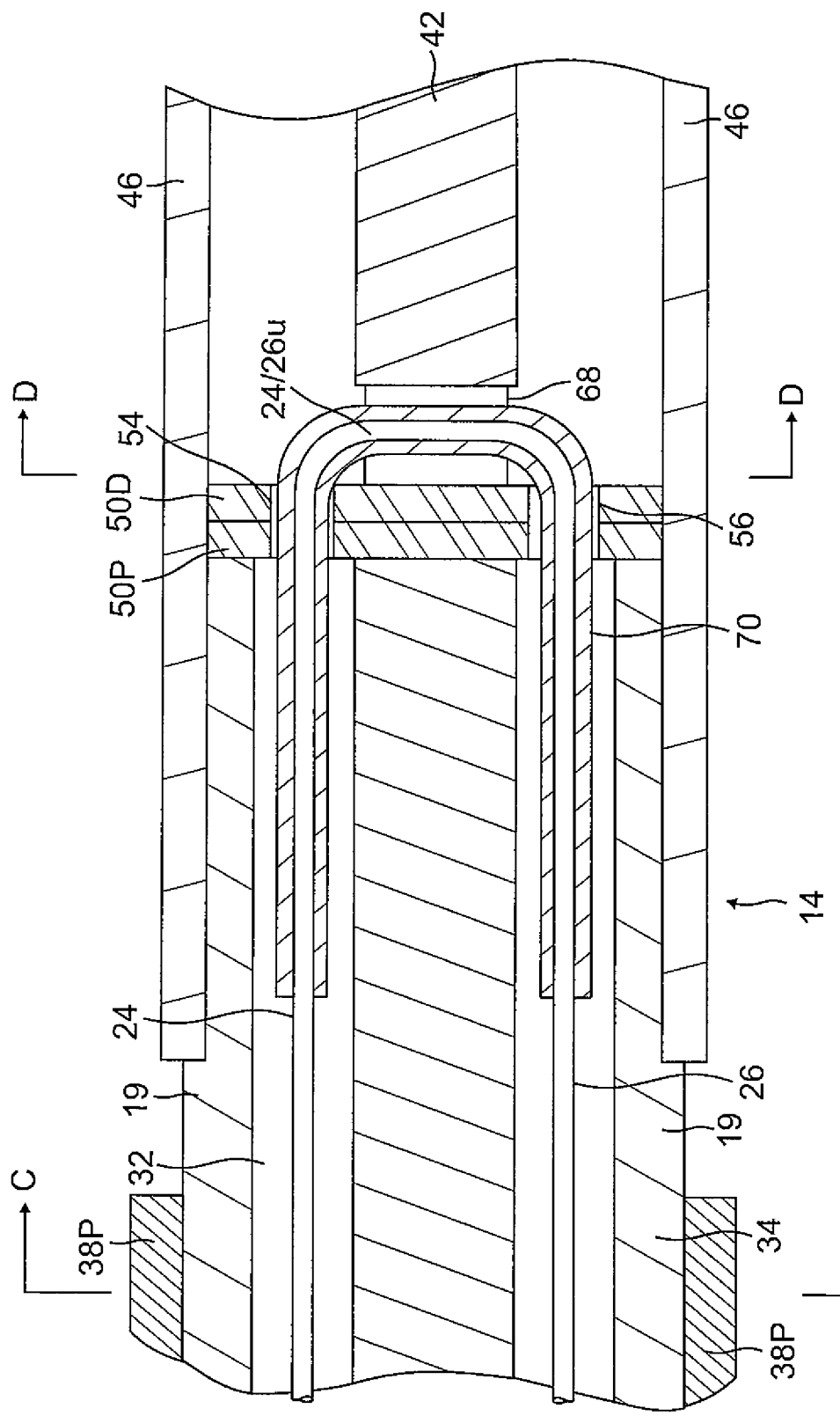
FIG. 3A is a side cross-sectional view of the catheter of FIG. 1, including a junction between the deflection section and a distal electrode assembly, taken along a first diameter.
Figure 3B:
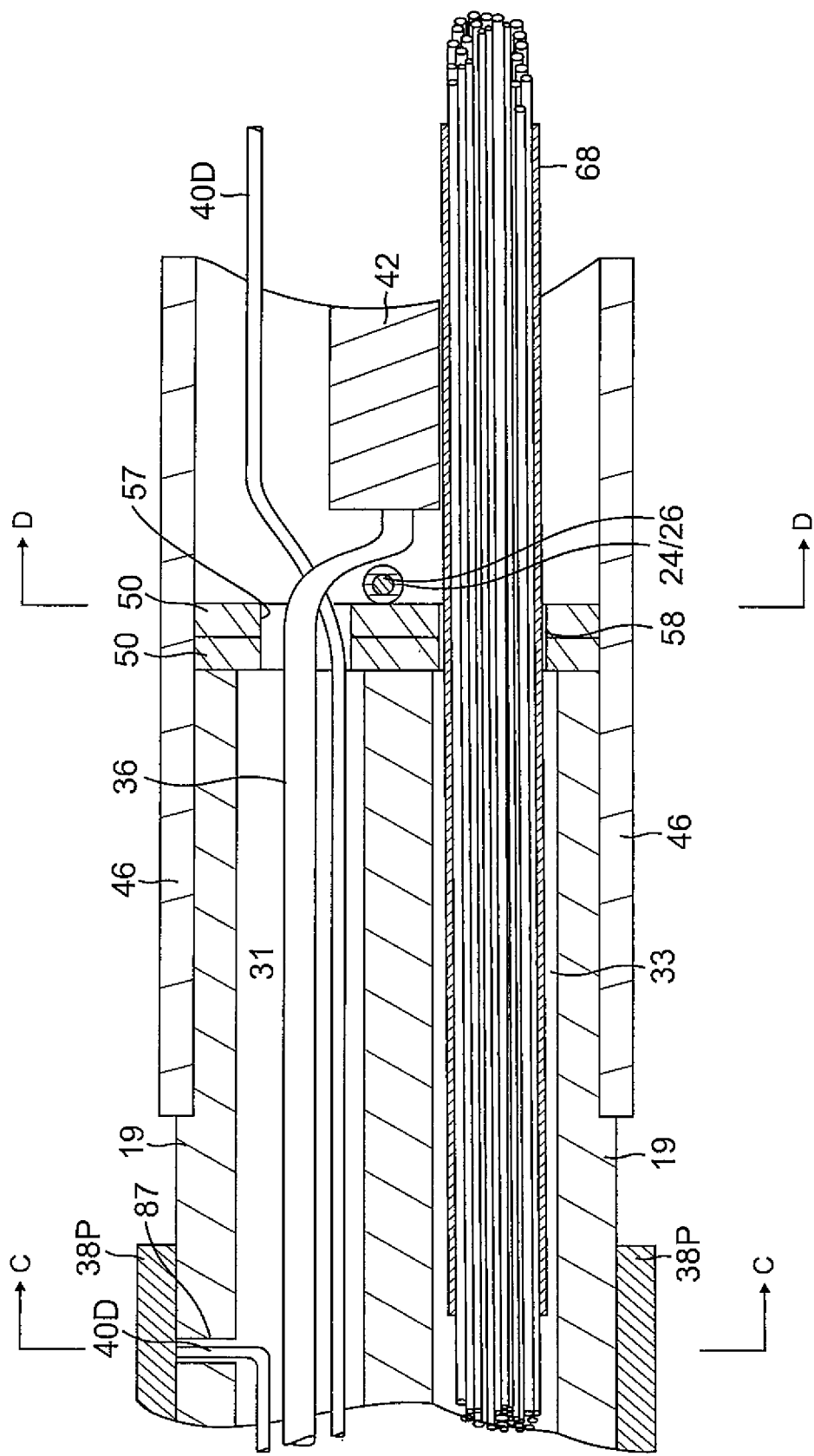
FIG. 3B is a side cross-sectional view of the junction of FIG. 3A, taken along a second diameter generally perpendicular to the first diameter.

As shown in FIGS. 3A and 3B, the distal electrode matrix 15 includes a connector tubing 26 mounted on a distal end of the tubing 19 of the intermediate section 14. The connector tubing 46 has a central lumen 48 to house various components. A means for attaching the connector tubing 46 and the intermediate section 14 comprises an outer circumferential notch 27 in the distal end of the tubing 19 that receives the inner surface of the proximal end of the connector tubing 46. The intermediate section 14 and connector tubing 46 are attached by glue or the like.

Figure 3C:
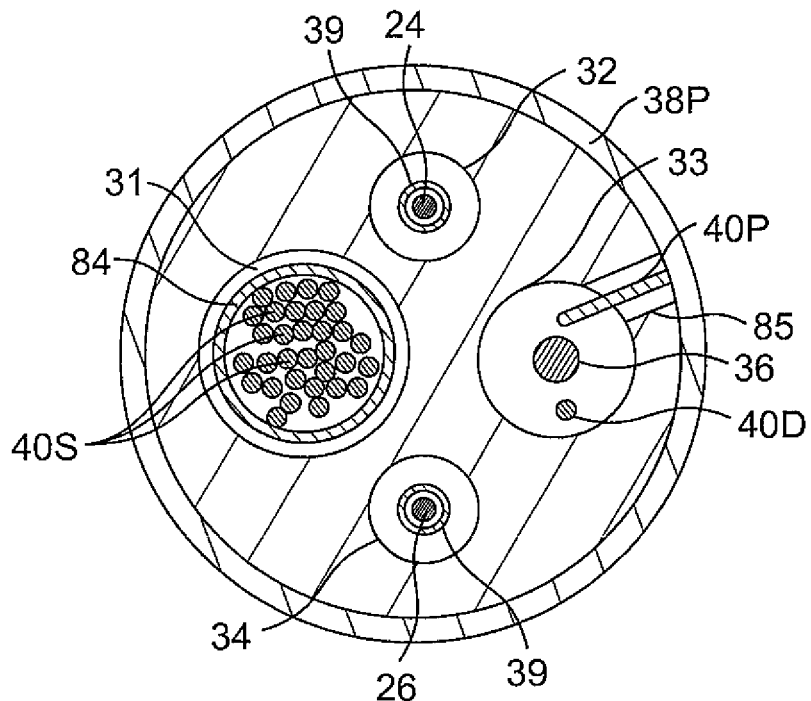
FIG. 3C is an end cross-sectional view of the deflection section of FIGS. 3A and 3B, taken along line C-C.
Figure 3D:
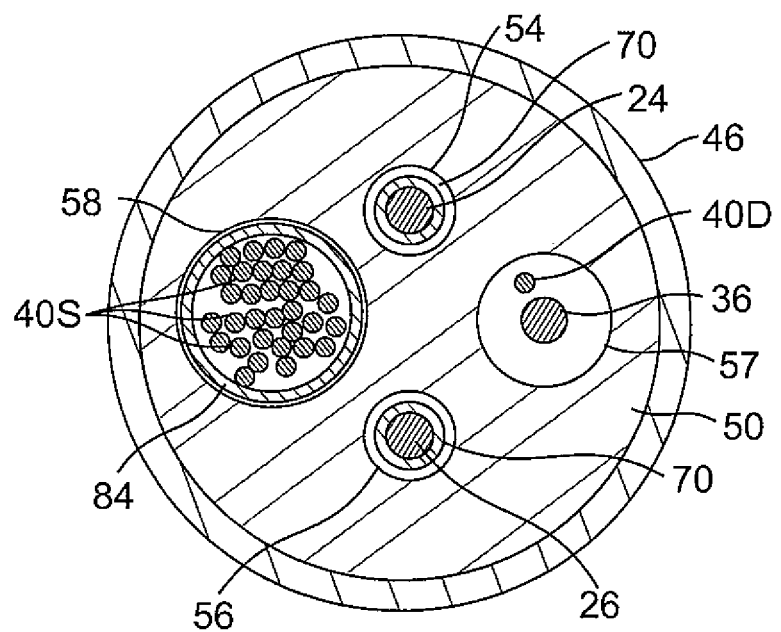
FIG. 3D is an end cross-sectional view of the junction of FIG. 3A, taken along line D-D.
Figure 4:
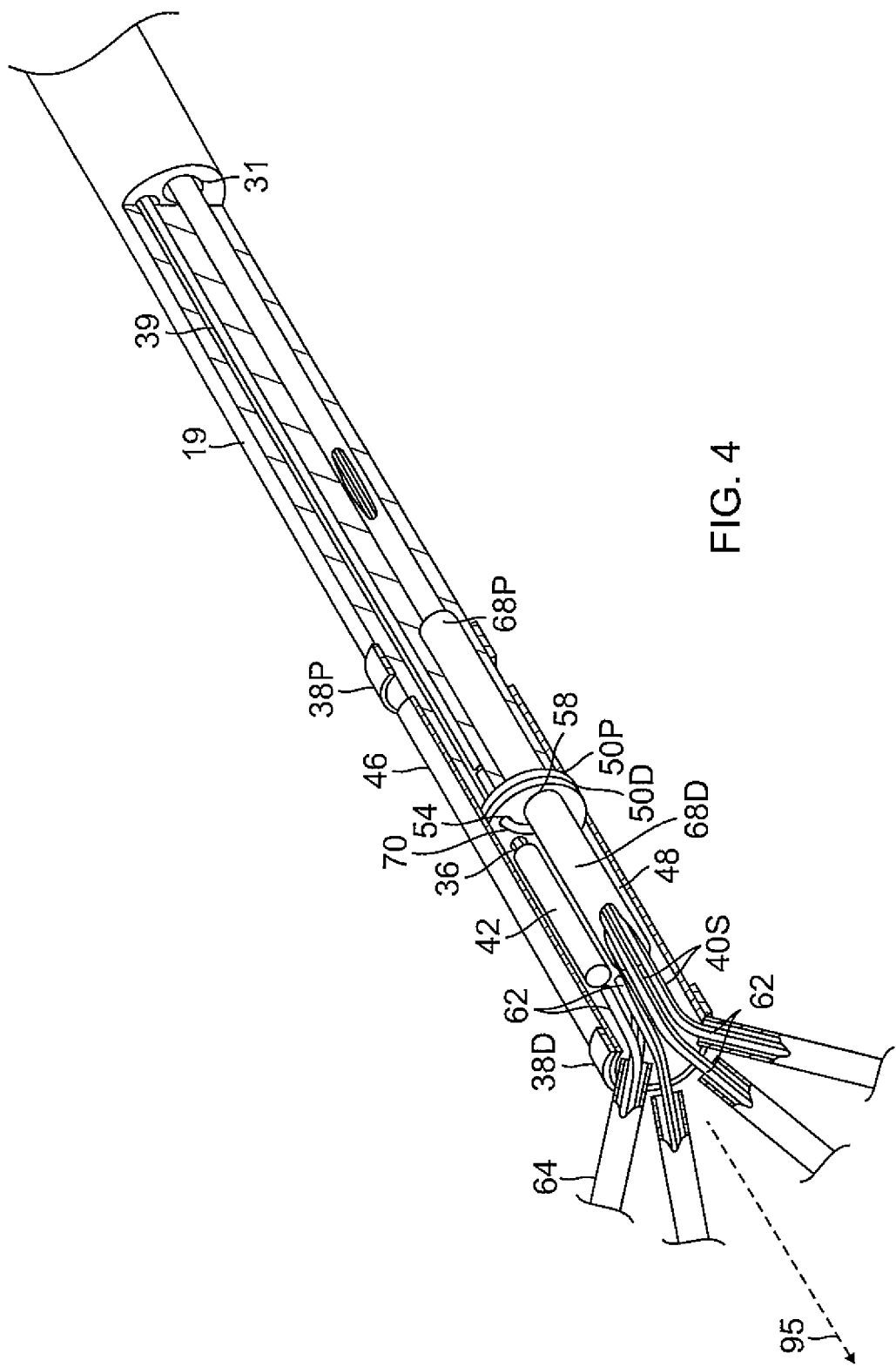
FIG. 4 is a perspective view of a junction between the deflection section and the distal electrode assembly, with parts broken away.

As also shown in FIG. 4, the connector tubing 46 houses various components, including the electromagnetic position sensor 42, and a distal anchor for the puller wires 24 and 26. In the disclosed embodiment, the distal anchor includes one or more washers, for example, a distal washer 50D and a proximal washer 50P, each of which has a plurality of matching axial through-holes that allow passage of components between the deflection section 14 and the connector tubing 46 while maintaining axial alignment of these components relative to the longitudinal axis 95 of the catheter 10. As also shown in FIG. 3D, the through-holes include holes 54 and 56 that are axially aligned with the second and fourth lumens 32 and 34 of the tubing 19, respectively, to receive a distal end of puller wires 24 and 26, respectively. It is understood that the puller wires 24 and 26 may actually form a single tensile member with a distal U-bend section that passes through the holes 54 and 56. With tension on the washers 50D and 50P exerted by the U-bend section of the puller wires 24 and 26, the washers firmly and fixedly abut against the distal end of the tubing 19 of the deflection section 14 to distally anchor the U-bend section.

As also shown in FIG. 3D, each washer also includes through-hole 58 which is axially aligned with the first lumen 31 and allows passage of the lead wires 40S from the deflection section 14 and into the lumen 48 of the connector tubing 46. Each washer further includes through-hole 57 which is axially aligned with the third lumen 33 and allows passage of the sensor cable 36 from the deflection section 14 into lumen 48 of the connector tubing 46 where the electromagnetic position sensor 42 is housed. The lead wire 40D also passes through the hole 57 to enter the lumen 48 for attachment to the distal ring electrode 38D carried on the outer surface of the connector tubing 46 via an opening (not shown) formed in the side wall of the connector tubing 46 through which a distal end of the lead wire 40D is welded or otherwise attached to the distal ring electrode 38D as known in the art. Carried on the outer surface of the tubing 19 near the distal end of the intermediate deflection section 14, a proximal ring electrode 38P is connected to lead wire 40P via an opening 87 (FIG. 3B) formed in the side wall of the tubing 19 that provides communication between the third lumen 33 and outside of the tubing 19. The distal end of the lead wire is welded or otherwise attached to the proximal ring electrode 38P as known in the art.

Extending from the distal end of the connector tubing 46 is the distal electrode matrix 15 with a plurality of spines 17 all extending generally in a common plane. Each spine 17 has a shorter proximal portion 17P and a longer distal portion 17D, wherein the distal portion of each spine is generally parallel with each other within the common plane. The plurality of spines may range between about 2 and 10, preferably between about 2 and 6, and more preferably about four. Each spine may have a length ranging between about 5 and 50 mm, preferably about 10 and 35 mm, and more preferably about 28 mm. The parallel distal portion 17D of each spine 17 may be spaced apart from each other by a distance ranging between about 1 mm and 20 mm, preferably about 2 and 10 mm, and more preferably about 4 mm.

As shown in FIG. 4, each spine has an elongated shape memory member 62 extending through the length of the spine. A proximal portion of each spine extends into a distal end portion of the connector tubing 46 and is anchored in the lumen 48. Each spine 17 also has a nonconductive covering 64 that covers the shape memory member 62 and each spine 17 carries a plurality of ring electrode 37 ranging between about 4 and 11, preferably about 6 and 9, and more preferably about 8. Accordingly, the distal electrode matrix 15 carries a plurality of electrodes ranging between about 20 and 44, preferably between about 28 and 36 electrodes, and more preferably about 32 electrodes. The surface area of the matrix 15 may range between about 1.5 $cm^2$ to 3.0 $cm^2$, preferably between about 1.9 $cm^2$ and 2.5 $cm^2$, and more preferably about 2.2 $cm^2$. In some embodiments, the electrode density is about 15 electrodes per square centimeter and dimensions of about 12 mm×18 mm.

With shape memory in its spines 17, the distal electrode matrix 15 can assume at least two configurations: a deployed configuration with the spines 17 splayed out in a common plane where the proximal portions 17P are angled and the distal portions 17D are generally parallel, and a collapsed configuration where the spines can be bundled generally along the longitudinal axis 95.

The support member 62 is made of a material having shape-memory, i.e., that can be temporarily straightened or bent out of its original shape upon exertion of a force and is capable of substantially returning to its original shape in the absence or removal of the force. One suitable material for the support member is a nickel/titanium alloy. Such alloys typically comprise about 55% nickel and 45% titanium, but may comprise from about 54% to about 57% nickel with the balance being titanium. A nickel/titanium alloy is nitinol, which has excellent shape memory, together with ductility, strength, corrosion resistance, electrical resistivity and temperature stability. The non-conductive covering 64 can be made of any suitable material, and is preferably made of a biocompatible plastic such as polyurethane or PEBAX. If desired, the support member 62 can be eliminated and the distal end of the non-conductive covering 64 can be pre-formed to have the desired curvature or configuration.

Each shape-memory support member 62 extending through its respective nonconductive covering 64 has a proximal end that is received and anchored in the distal end of the connector tubing 46 by polyurethane 67 or the like. Lead wires 40S for the spine electrodes 37 extend through a protective distal polytube 68D distal of the washer 50D. They diverge at the distal end of the connector tubing 46, and extend alongside their respective shape memory member 62, into their respective nonconductive covering 64 of their respective spines 17. Each lead wire 40S is connected to its respective spine ring electrode 37 via a respective opening (not shown) formed in the side wall of the covering 64 through which a distal end of the lead wire reaches outside of the covering 64 and is welded or otherwise attached to its spine ring electrode 37, as known in the art.

At the junction of distal electrode matrix 15 and the connector tubing 46, the non-conductive covering 64 of each spine 17 is attached and sealed at its proximal end to the tubing 46 by the polyurethane 67 or the like. If desired, the proximal ends of the support members 62 can extend further proximally into the connector tubing 46. Polyurethane 71 or the like is also applied to the distal end of each spine to seal the distal end and provide an atraumatic dome.

Figure 5:
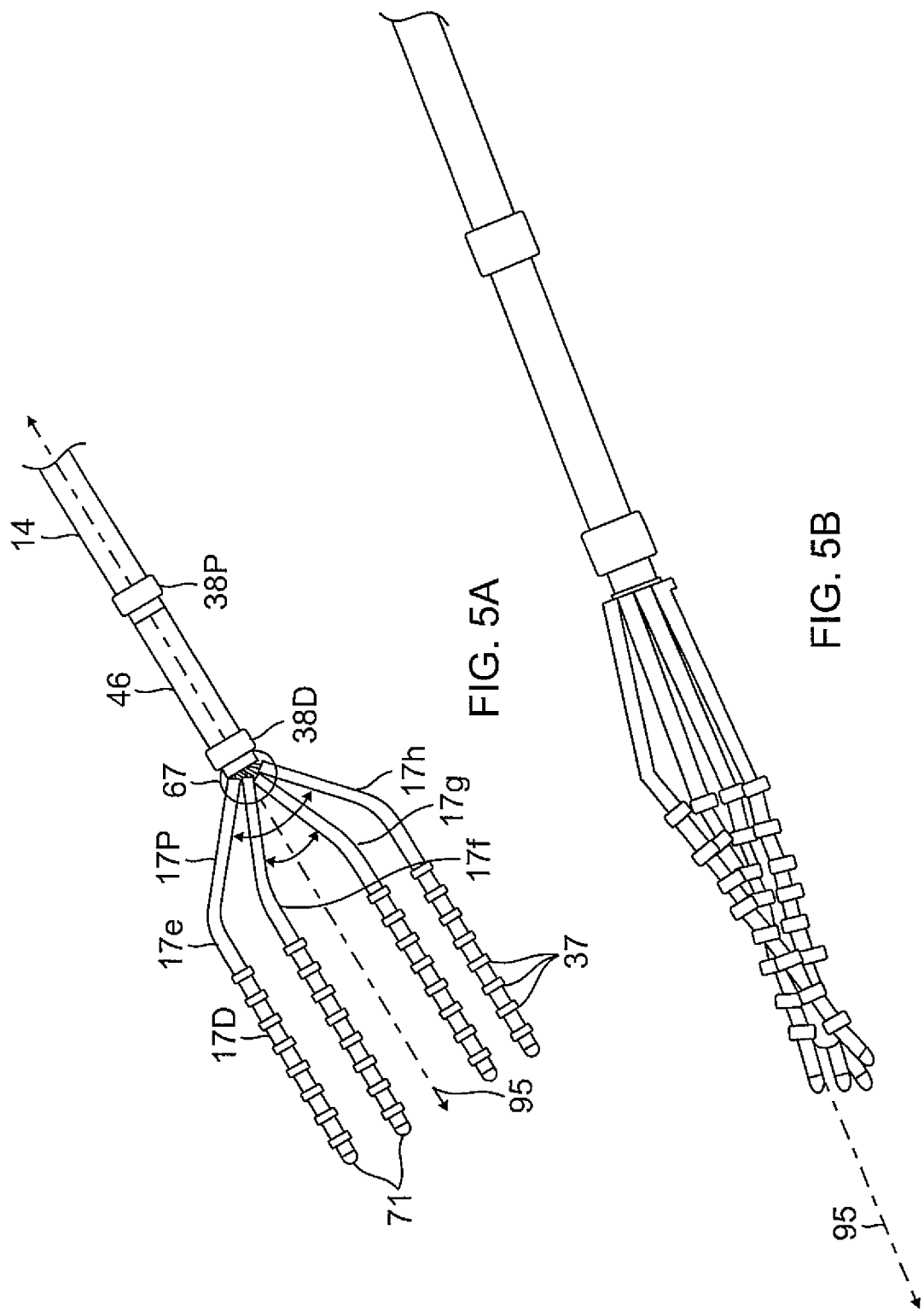
FIG. 5A is a side view of a distal electrode assembly in a deployed configuration.
FIG. 5B is a side view of the distal electrode assembly of FIG. 5A in a collapsed configuration.

As mentioned above, the matrix 15 can assume at least two configurations: a deployed, expanded configuration (FIG. 5A) and a collapsed configuration (FIG. 5B). With the matrix in the deployed, expanded configuration, the proximal portion 17P of each spine splays out and extends generally in a common plane, with the outer spines 17e and 17h spreading outwardly at a greater angle away from the longitudinal axis 95 of the catheter and the inner spines 17f and 17g spreading outwardly at a lesser angle away from the longitudinal axis 95, whereas the distal portion 17D of each spine extends generally parallel to each other and the longitudinal axis 95, within the common plane. With the matrix in the collapsed configuration (FIG. 5B), spines are bundled. The proximal portions 17P the spines 17e, 17f, 17g, and 17h are gathered and closer to each other along the longitudinal axis 95, and the distal portions 17D are also gathered and substantially closer to each other along the longitudinal axis 95. The collapsed configuration facilitates the spines 17 and hence the matrix 15 to be fed into a guiding sheath.

The proximal ends of the lead wires 40S and 40D and 40P are electrically connected to a suitable connector (not shown) in the distal end of the control handle 16, which is connected to a source of ablation energy, e.g., RF energy, as is known in the art. The lead wires 40S and 40R extend through the central lumen 18 of the catheter body 12. The lead wires 40S extend through the first lumen 31 of the tubing 19 of the intermediate section 14, and the lead wires 40R extend through the third lumen 33 of the tubing 19. Passing through the holes 58 in the washers 50D and 50P, the lead wires 40S extend through a protective proximal polytube 68 which protects them from being damaged by the hole 58 in the washers.

In the depicted embodiment, the lead wires 40S extending through the central lumen 18 of the catheter body 12 and the first lumen 31 in the deflection section 14 may be enclosed within a protective sheath 84 to prevent contact with other components in the catheter. The protective sheath can be made of any suitable material, preferably polyimide. As would be recognized by one skilled in the art, the protective sheath can be eliminated if desired.

The ring electrodes 37 and 38D and 38P can be made of any suitable solid conductive material, such as platinum or gold, preferably a combination of platinum and iridium, and mounted onto the non-conductive cover 64 and the connector tubing 46 with glue or the like. Alternatively, the ring electrodes can be formed by coating the non-conductive cover 64 and connector tubing 46 with an electrically conducting material, like platinum, gold and/or iridium. The coating can be applied using sputtering, ion beam deposition or an equivalent technique.

The ring electrodes 37 on the spines 17 can be approximately evenly spaced along each spine. They may form any desirable pattern, for example, a "rectangular grid" pattern (FIG. 5A)

In another embodiment, each spine may have "paired" electrodes comprising of pairs of closely-spaced ring electrodes. As used herein, the term "ring electrode pair" refers to a pair of ring electrodes that are arranged closer to each other than they are to the other adjacent ring electrodes. In some embodiments, the distance between two electrodes of an electrode pair is less than about 3 mm, more preferably less than about 2 mm, still more preferably from about 0.5 mm to about 1.5 mm. The number of electrode pairs can vary as desired, and preferably ranges from 3 to 7 pairs, more preferably 5 pairs.

The distal section 15 may carry, for example, 20 (4 pairs of electrodes×5 spines) with a space of approximately 1 mm between the two electrodes of each pair. Preferably each ring electrode is relatively short, having a length ranging from about 0.4 mm to about 0.75 mm. Regardless of the size and number of the ring electrodes, the electrode pairs are preferably approximately evenly spaced along the distal section 15. The closely-spaced electrode pairs allow for more accurate detection of near field pulmonary vein potential versus far field atrial signals, which is very important when trying to treat atrial fibrillation. Specifically, the near field pulmonary vein potentials are very small signals whereas the atria, located very close to the pulmonary vein, provides much larger signals. Accordingly, even when the mapping array is placed in the region of a pulmonary vein, it can be difficult for the physician to determine whether the signal is a small, close potential (from the pulmonary vein) or a larger, farther potential (from the atria). Closely-spaced bipoles permit the physician to more accurately determine whether he is looking at a close signal or a far signal. Accordingly, by having closely-spaced electrodes, one is able to target exactly the locations of myocardial tissue that have pulmonary vein potentials and therefore allows the clinician to deliver therapy to the specific tissue. Moreover, the closely-spaced electrodes allow the physician to determine the exact anatomical location of the ostium/ostia by the electrical signal.

An electromagnetic position sensor 42 is housed in the lumen of the nonconductive covering 46 (FIG. 4). The sensor cable 36 extends from a proximal end of the position sensor 42, and through the hole 57 of the washers 50, the third lumen 33 of the tubing 19 of the deflection section 14, and the central lumen 18 of the catheter body 12. The cable is attached to a PC board in the control handle 16, as known in the art.

The puller wires 24 and 26 (whether as two separate tensile members or parts of a single tensile member) are provided for bi-directional deflection of the intermediate section 14. The puller wires 24 and 26 are actuated by mechanisms in the control handle 16 that are responsive to a thumb control knob or a deflection control knob 11. Suitable control handles are disclosed in U.S. Pat. Nos. 6,123,699; 6,171,277; 6,183,435; 6,183,463; 6,198,974; 6,210,407 and 6,267,746, the entire disclosures of which are incorporated herein by reference.

As shown in FIG. 2A, the puller wires 24 and 26 extend through the central lumen 18 of the catheter body 12 and through the second and fourth lumens 32 and 34, respectively, of the tubing 19 of the deflection section 14. As shown in FIGS. 3A and 3C, they extend through holes 54 and 56, respectively of the washers 50. Where the puller wires are part of a single tensile member, the single tensile member has a U-bend 24/26U (FIG. 3A) at the distal face of the distal washer which anchors the distal ends of the puller wires. In that regard, the U-bend extends through a short protective tubing 70 to protect the puller wires from the holes 54 and 56. Alternatively, where the puller wires are separate tensile members, their distal ends may be anchored via T-bars, as known in the art and described in, for example, U.S. Pat. No. 8,603,069, the entire content of which is incorporated herein by reference. In any case, the puller wires 24 and 26 are made of any suitable metal, such as stainless steel or Nitinol, and each is preferably coated with TEFLON or the like. The coating imparts lubricity to the puller wires. The puller wires preferably have a diameter ranging from about 0.006 to about 0.010 inch.

A compression coil 66 is situated within the central lumen 18 of the catheter body 12 in surrounding relation to each puller wire 24, as shown in FIG. 2B. Each compression coil 66 extends from the proximal end of the catheter body 12 to the proximal end of the intermediate section 14. The compression coils 66 are made of any suitable metal, preferably stainless steel. Each compression coil 66 is tightly wound on itself to provide flexibility, i.e., bending, but to resist compression. The inner diameter of the compression coil 66 is preferably slightly larger than the diameter of its puller wire. The Teflon coating on each puller wire allows it to slide freely within its compression coil. The outer surface of each portion of the compression coil 66 through second and fourth lumens 32 and 34 of the deflection section 14 is covered by a flexible, non-conductive sheath 68, e.g., made of polyimide tubing.

The compression coil 66 is anchored at its proximal end to the outer wall 20 of the catheter body 12 by a proximal glue joint (not shown) and at its distal end to the intermediate section 14 by a distal glue joint 92. Both glue joints may comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 20 of the catheter body 12 which is heated sufficiently to form a permanent hole. The glue is then introduced through the hole to the outer surface of the compression coil 66 and wicks around the outer circumference to form a glue joint about the entire circumference of the compression coil.

Within the second and fourth lumens 32 and 34 of the intermediate section 14, each puller wire 24 and 26 extends through a plastic, preferably Teflon, puller wire sheath 39, which prevents the puller wires from cutting into the wall of the tubing 19 of the deflection section 14 when the deflection section is deflected.

Figure 6:
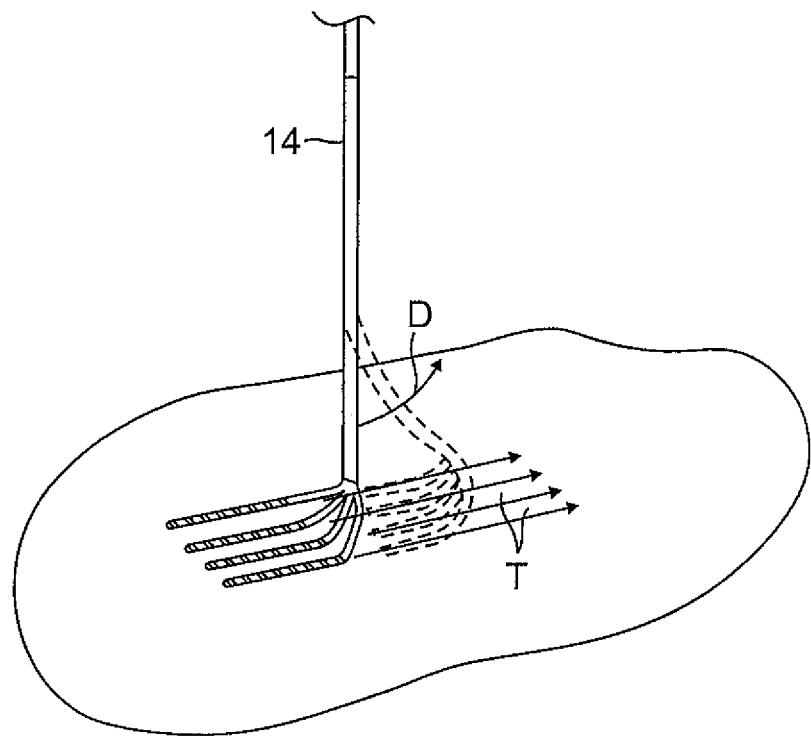
FIG. 6 is a schematic drawing illustrating a method of using the catheter of the present invention, according to some embodiments.

In use, a suitable guiding sheath (not shown) is inserted into the patient with its distal end positioned at or near a desired tissue location for diagnostics such as mapping and/or treatment such as ablation. An example of a suitable guiding sheath for use in connection with the present invention is the Preface Braided Guiding Sheath, commercially available from Biosense Webster, Inc. (Diamond Bar, Calif.). The catheter 10 is passed through the guiding sheath and advanced therethrough to the desired tissue location. In particular, the spines 17 of the distal electrode matrix 15 are collapsed and straightened, as shown in FIG. 5A, and fed into the proximal end of the guiding sheath. After the distal electrode matrix 15 has reached the desired tissue location, the guiding sheath is pulled proximally, exposing at least the spines 17, if not also the deflectable intermediate section 14, as needed. Outside of the guiding sheath 36, the spines 17 assume the deployed configuration where the proximal portion 17P of each spine splays out and extends generally in a common plane, with the outer spines 17e and 17h spreading outwardly at a greater angle away from the longitudinal axis 95 of the catheter and the inner spines 17f and 17g spreading outwardly at a lesser angle away from the longitudinal axis 95, and the distal portion 17D of each spine extending parallel to each other within the plane, as shown in FIG. 5A. The matrix has a first side and a second side. As shown in FIG. 6, the user places the first side against the tissue surface, with at least the intermediate section 14 (if not also a distal portion of the catheter body 12) generally perpendicular to the tissue surface, and actuates the control handle to deflect the intermediate deflection section 14 (arrow D) such that the first side deflects toward the catheter, which drags the first side of the distal spine portions 17D across the tissue surface as the section 14 is deflecting. The distal spine portions 17D drag across the tissue surface while remaining generally parallel to each other along tracks T which are generally linear and parallel, and in the same direction as the deflection direction D.

Figure 7:
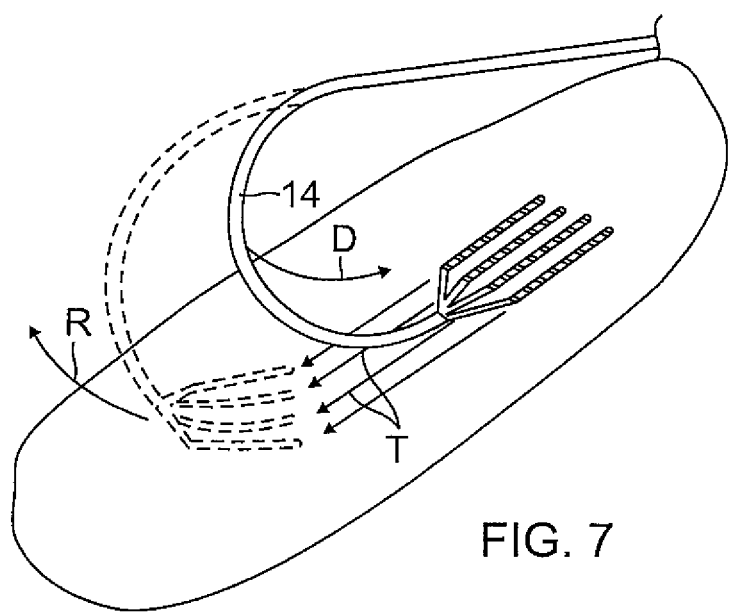
FIG. 7 is a schematic drawing illustrating a method of using the catheter of the present invention, according to another embodiment.

Alternatively, as shown in FIG. 7, the user actuates the control handle to deflect the section 14 along direction D with the electrode matrix first surface deflected toward the catheter. The user then positions at least the distal portion of the catheter body 12 generally parallel with the tissue surface and places the electrode matrix second surface against the tissue surface. The user then releases the deflection (along opposite direction R) which drags the second surface of the distal spine portions 17D across the tissue surface as the deflection section 14 straightens. The distal spine portions 17D drag across the tissue surface while remaining generally parallel to each other along tracks T which are generally linear and parallel, and in the direction R opposite to the deflection direction D.

In either manner, the spine electrodes 37 are in contact with the tissue surface generally maintaining a consistent separation spacing from each other within the distal electrode matrix as the spines are dragged across the tissue surface for high density electrode sensing and uniform and predictable mapping. In accordance with a feature of the invention, the matrix has an "n×m" electrode layout or arrangement, for example, four spines, with eight electrodes on each spine, for a total of 32 closely-spaced spine electrodes for mapping.

In some embodiments, the distal and proximal ring electrodes 38D and 38P serve as reference electrodes for visualization of the catheter on a 3-D mapping system, such as CARTO® 3 SYSTEM available from Biosense Webster, Inc., which automatically locates the EM sensor 42, processes reference location values from electrodes 38D and 38P, which are at a constant location from the EM sensor 42 and determines the location of the spine electrodes 37 and visualizes the remainder of the electrode matrix 15.

Figure 8C:
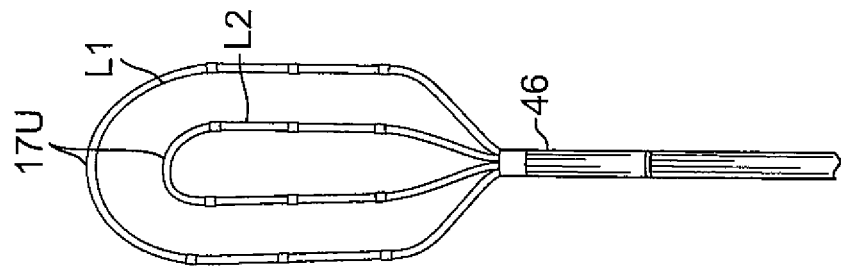
FIGS. 8A-8F illustrate distal electrode assemblies in accordance with additional embodiments of the present invention.
Figure 8B:
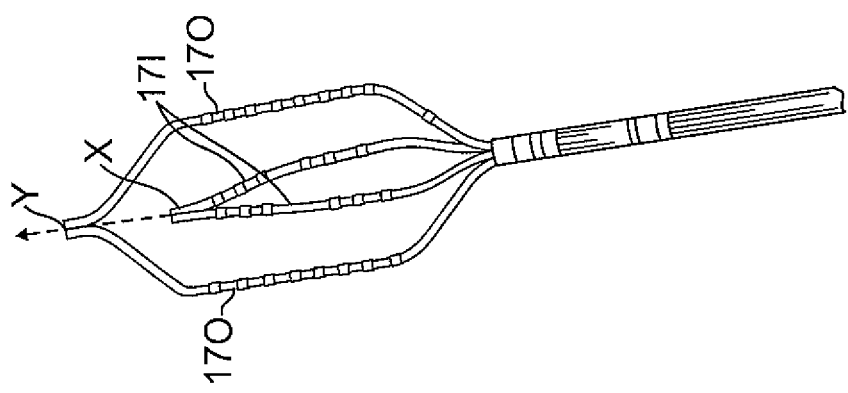
Figure 8A:
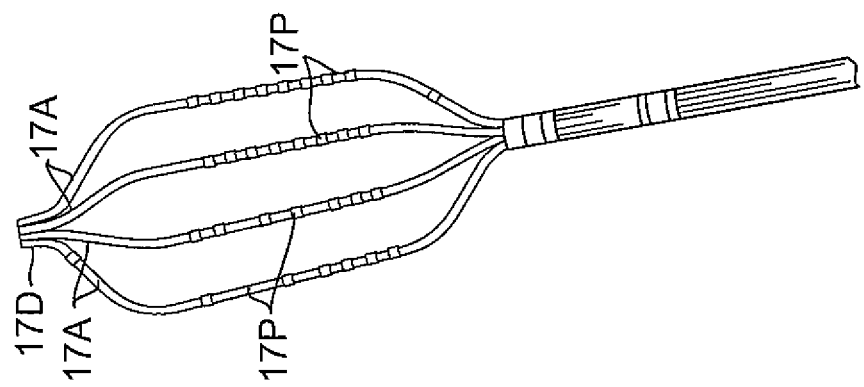
Figure 8F:
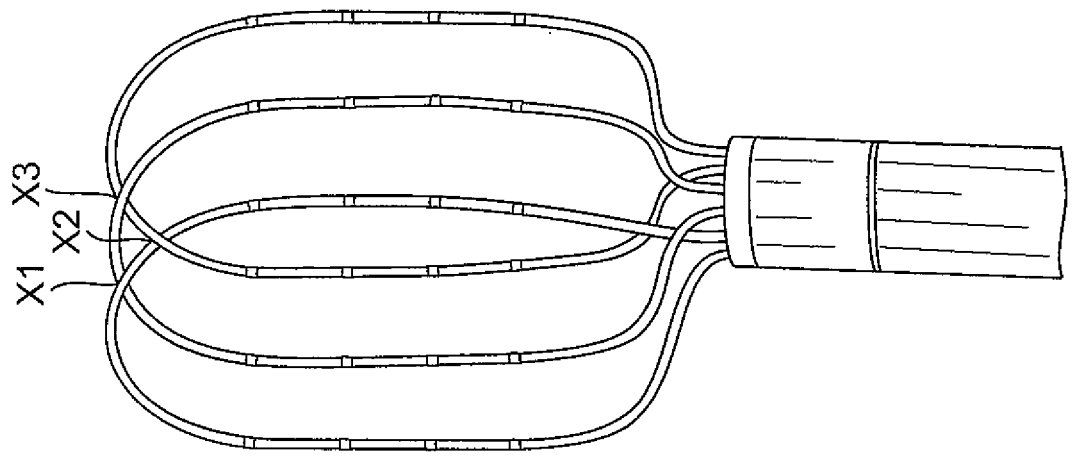
Figure 8E:
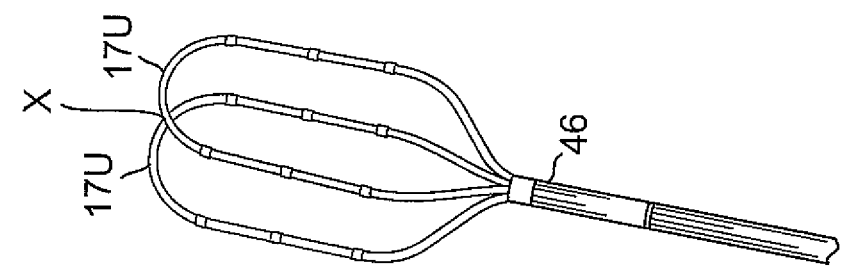
Figure 8D:
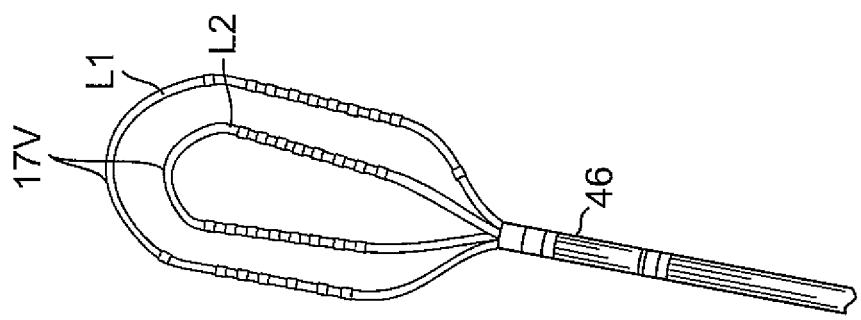

Additional embodiments of a catheter of the present invention are shown in FIGS. 8A-8F. In each of the distal electrode arrays, the spines form closed loops lying in a common plane, having no free distal ends, where the distal end of each spine is joined with or extends to the distal end of at least one other spine in a manner which maintains the spines in a generally parallel position or at least in a manner which generally maintains a predetermined spacing between the spines. By keeping the spines separated and equidistant from each other, the spines are less prone to overlap and the electrodes are less susceptible to "cross talk," without compromising the flexibility of the spines. As shown in FIG. 8A, the spines of the array may have angled distal portions 17A that converge and allow distal ends 17D of all the spines of the array to meet and be joined together while keeping the proximal portion 17P of the spines generally parallel and equidistant. As shown in FIG. 8B, the spines are arranged similarly as the spines of FIG. 8A, although the distal ends of outer spines 17O are joined only with each other and the distal ends of inner spines 17I are joined only with each other, and joined distal ends of the outer spines 17O are joined at a location Y distal of a location X at which the distal ends of the inner spines 17I are joined along the longitudinal axis of the array. As shown in FIG. 8C-8F, the spines of the array are looped such that a pair of spaced-apart spines are formed from a single continuous spine turned back on itself with a U-section 17U its two ends anchored in the distal end of the connector tubing 46. In the arrays of FIGS. 8C and 8D, the length of each continuous spine is different with one greater length forming a larger loop L1 and one shorter length forming a smaller loop L2, wherein the smaller loop is inside and surrounded by the larger loop. In the array of FIG. 8C, the spacing between the inner and outer loops along the linear portions of the loops are generally uniform, whereas in the array of FIG. 8D, the spacing between the inner and outer loops along the linear portions of the loops varies, and the turned-back section is more angular, like a V-section 17V rather than a U-section. In the array of FIG. 8E, the lengths are the same such that the loops are generally the same size. In addition, the loops are offset from each other such that they intersect at a single location X. In the array of FIG. 8F, the spines are arranged similarly to the spines of FIG. 8E, although there are more than two intersecting loops, for example, three intersecting loops, with three intersecting locations X1, X2, and X3. As shown in FIG. 8F, each of the three (or more) loops are offset from each other such that they intersect each other at the intersecting locations X1, X2 and X3. The locations of the intersections may be fixed with glue or fastened by brackets or knots, or the nonconductive cover of the spines may be heat bonded or melted together.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Also, different features of different embodiments may be combined as needed or appropriate. Moreover, the catheters described herein may be configured to apply various energy forms, including microwave, laser, RF and/or cryogens. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
    an elongated catheter body defining a longitudinal axis; and
    a generally planar distal electrode assembly distal of the catheter body, the distal electrode assembly comprising a plurality of spines including a first spine and a second spine,
        the first spine including a first first-spine linear portion, a second first-spine linear portion, and a first V-shaped distal portion connecting the first first-spine linear portion, and the second first-spine linear portion, and
        the second spine including a first second-spine linear portion, a second second-spine linear portion, and a second V-shaped distal portion connecting the first second-spine linear portion and the second second-spine linear portion, the second V-shaped distal portion being offset from the first V-shaped distal portion.

2. The catheter of claim 1, in which the first spine comprises a first single continuous spine loop and the second spine comprises a second single continuous spine loop.

3. The catheter of claim 2, in which the first first-spine linear portion, the second first-spine linear portion, the first second-spine linear portion, and the second second-spine linear portion each include at least four electrodes that are spaced apart at generally equal distances from each other such that the first spine and second spine together comprise at least sixteen electrodes disposed in a rectangular grid pattern.

4. The catheter of claim 3, in which the first first-spine linear portion comprises four electrodes, the second first-spine linear portion comprises four electrodes, the first second-spine linear portion comprises four electrodes, and the second second-spine linear portion comprises four electrodes.

5. The catheter of claim 3, in which a spacing between the first first-spine linear portion and the first second-spine linear portion varies along the first first-spine linear portion and the first second-spine linear portion.

6. The catheter of claim 3, in which the first spine loop is larger than the second spine loop.

7. The catheter of claim 6, in which the second spine loop is inside and surrounded by the first spine loop.

8. The catheter of claim 7, in which the first V-shaped distal portion is disposed distal to the second V-shaped distal portion.

9. The catheter of claim 3, in which the first V-shaped distal portion intersects the second V-shaped distal portion at a first intersecting location.

10. The catheter of claim 9, in which the plurality of spines further comprises a third spine including a first third-spine linear portion, a second third-spine linear portion, and a third V-shaped distal portion connecting the first third-spine linear portion and the second third-spine linear portion, the third V-shaped distal portion being offset from the first V-shaped distal portion and the second V-shaped distal portion.

11. The catheter of claim 10, in which the third spine comprises a third single continuous spine loop.

12. The catheter of claim 11, in which the first third-spine linear portion and the second third-spine linear portion each include at least four electrodes that are spaced apart at generally equal distances from each other such that the first spine, the second spine, and the third spine together comprise at least twenty-four electrodes disposed in a rectangular grid pattern.

13. The catheter of claim 12, in which the first first-spine linear portion comprises four electrodes, the second first-spine linear portion comprises four electrodes, the first second-spine linear portion comprises four electrodes, the second second-spine linear portion comprises four electrodes, the first third-spine linear portion comprises four electrodes, and the second third-spine linear portion comprises four electrodes.

14. The catheter of claim 12, in which the third V-shaped distal portion intersects the first V-shaped distal portion at a second intersecting location, and the third V-shaped distal portion intersects the second V-shaped distal portion at a third intersecting location.

15. The catheter of claim 14, in which the first V-shaped distal portion is attached to the second V-shaped distal portion at the first intersecting location, the third V-shaped distal portion is attached to the first V-shaped distal portion at the second intersecting location, and the third V-shaped distal portion is attached to the second V-shaped distal portion at the third intersecting location.

* * * * *